US 8,636,650 B2

(12) United States Patent
Lee

(10) Patent No.: US 8,636,650 B2
(45) Date of Patent: Jan. 28, 2014

(54) CAPSULE-TYPE IMAGE PHOTOGRAPHING APPARATUS AND ENDOSCOPY USING THE SAME

(75) Inventor: Jong-Jin Lee, Seoul (KR)

(73) Assignee: Kolen Co., Ltd., Gyeonggi-do (KR)

( * ) Notice: Subject to any disclaimer, the term of this patent is extended or adjusted under 35 U.S.C. 154(b) by 144 days.

(21) Appl. No.: 12/515,953

(22) PCT Filed: Nov. 21, 2007

(86) PCT No.: PCT/KR2007/005854
§ 371 (c)(1),
(2), (4) Date: May 22, 2009

(87) PCT Pub. No.: WO2008/062997
PCT Pub. Date: May 29, 2008

(65) Prior Publication Data
US 2010/0056864 A1  Mar. 4, 2010

(30) Foreign Application Priority Data
Nov. 22, 2006  (KR) .................. 10-2006-0116011

(51) Int. Cl.
*A61B 1/00* (2006.01)
(52) U.S. Cl.
USPC ...................... 600/109; 600/113; 600/130
(58) Field of Classification Search
USPC ............ 600/109, 113, 302, 407, 476; 396/14, 396/17
See application file for complete search history.

(56) References Cited

U.S. PATENT DOCUMENTS

| | | | |
|---|---|---|---|
| 6,855,111 B2* | 2/2005 | Yokoi et al. | 600/179 |
| 7,485,093 B2* | 2/2009 | Glukhovsky | 600/160 |
| 2003/0158503 A1* | 8/2003 | Matsumoto | 600/593 |
| 2005/0054901 A1* | 3/2005 | Yoshino | 600/176 |
| 2005/0085697 A1 | 4/2005 | Yokoi et al. | |
| 2005/0165272 A1* | 7/2005 | Okada et al. | 600/114 |
| 2006/0004255 A1 | 1/2006 | Iddan et al. | |
| 2006/0056828 A1* | 3/2006 | Iddan et al. | 396/14 |

FOREIGN PATENT DOCUMENTS

| | | |
|---|---|---|
| JP | 09-327447 A | 12/1997 |
| JP | 2005-080790 A | 3/2005 |

(Continued)

OTHER PUBLICATIONS

Japanese Office Action dated Oct. 9, 2012; Appln. No. 2009-538327.

*Primary Examiner* — John P Leubecker
*Assistant Examiner* — Arnaldo Torres Diaz
(74) *Attorney, Agent, or Firm* — Ladas & Parry LLP

(57) ABSTRACT

Provided are a capsule-type image photographing apparatus and endoscopy using the same. The apparatus includes a shell unit having a globular shape and a main body unit capable of freely rotating in the shell unit. The main body unit includes an image photographing system, a wireless transmitter, a battery, a counterweight for determining the center of gravity of the main body unit, and an encapsulant for fixing the image photographing system, the wireless transmitter, the battery, and the counterweight. The apparatus may be a long-distance capsule-type image photographing apparatus or a short-distance capsule-type image photographing apparatus depending on the position of the counterweight. By use of the long- and short-distance capsule-type image photographing apparatuses, the interior of the tested person's body can be effectively photographed.

8 Claims, 8 Drawing Sheets

(56) References Cited

FOREIGN PATENT DOCUMENTS

| | | |
|---|---|---|
| JP | 2006-271492 A | 10/2006 |
| KR | 2003-0025222 A | 3/2003 |
| KR | 10-0457752 B1 | 12/2004 |
| WO | 01/65995 A2 | 9/2001 |
| WO | WO 2004028335 A2 * | 4/2004 |

* cited by examiner

CAPSULE-TYPE IMAGE PHOTOGRAPHING APPARATUS AND ENDOSCOPY USING THE SAME

TECHNICAL FIELD

The present invention relates to a capsule-type image photographing apparatus and endoscopy using the same, and more particularly, to a capsule-type image photographing apparatus, which can control a photographing direction and photograph long-distance or short-distance regions, and endoscopy using the same apparatus.

BACKGROUND ART

A tube-type endoscope may inflict great pain and discomfort on a tested person during endoscopy. In order to remove the disadvantages of the tube-type endoscope, a capsule-type internal image photographing apparatus (hereinafter, a capsule-type endoscope) has been developed.

When a tested person swallows a capsule-type endoscope like a pill, the interior of internal organs is photographed by the capsule-type endoscope, and photographed data is stored in an additional storage device. After photographing is finished, a medical doctor may confirm the photographed data using a computer.

FIG. 1 is a cross-sectional view of a capsule-type endoscope that has been disclosed in Korean Patent Laid-open Publication No. 2003-0025222 entitled 'Internal image photographing apparatus and system' (hereinafter referred to as a conventional endoscope 200).

Referring to FIG. 1, the conventional endoscope 200 includes an image photographing system 130, which is comprised of a light source 100, a complementary metal oxide semiconductor (CMOS) image sensor (CIS) 110, and a lens 120. The light source 100 functions to irradiate light to an inner wall of the internal organ. The light source 100 is a light emitting diode (LED). Also, the lens 120 functions to condense light reflected by the inner wall of the internal organ on the CIS 110. The CIS 110 functions to convert an image received via the lens 120 into an electric signal. The conventional capsule-type endoscope 200 further includes a pair of batteries 140 for supplying power and a wireless transmitter 150 for transmitting an image signal detected by the CIS 110 to an external wireless image recording apparatus. The image photographing system 130, the batteries 140, and the wireless transmitter 150 are hermetically sealed by an exterior material 160. In this case, the exterior material 160 includes a dome-shaped transparent plastic material for enclosing the image photographing system 130 and a metal material for enclosing the batteries 140 and the wireless transmitter 150.

When a tested person swallows the conventional capsule-type endoscope, the capsule-type endoscope may give an extraneous feeling to the tested person. Also, the conventional capsule-type endoscope may have the following problems.

First, since the conventional capsule-type endoscope can photograph only long-distance regions, regions to be photographed may be limited. For example, when the interior of an internal organ having a wide internal space, such as the stomach, is photographed using the conventional capsule-type endoscope, it is difficult to photograph regions of the stomach near the endoscope. Even if the regions of the stomach near the conventional capsule-type endoscope are photographed, it is difficult to obtain significant information from low-resolution photographed images. Also, it is impossible to photograph regions to be seen in a reverse direction to a direction in which the endoscope proceeds. Also, since the conventional capsule-type endoscope passes through the stomach in a short amount of time, it is also difficult to take high-resolution images of long-distance regions.

Second, the conventional capsule-type endoscope has no directionality. In other words, the conventional capsule-type endoscope moves passively according to the peristalsis of the internal organ, which thereby substantially determines the direction of the lens 120 and the CIS 110. As a consequence, the image photographing system 130 of the conventional capsule-type endoscope photographs images in an arbitrary direction, so that it is difficult to photograph desired portions.

Third, when using the conventional capsule-type endoscope, it is troublesome for a tested person to carry an additional image storage device for a long amount of time in order to store photographed images. Furthermore, since the image storage device is expensive, it may be an economical burden on the tested person.

DISCLOSURE OF INVENTION

Technical Solution

The present invention provides a capsule-type image photographing apparatus, which can control a direction in which an image photographing system photographs images, and photograph long-distance or short-distance regions.

Also, the present invention provides an endoscopy method using the capsule-type image photographing apparatus according to the present invention.

According to an aspect of the present invention, there is provided a capsule-type image photographing apparatus including: a shell unit having a globular shape; and a main body unit capable of freely rotating in the shell unit. The main body unit comprises an image photographing system, a wireless transmitter, a battery, a counterweight for determining the center of gravity of the main body unit, and an encapsulant for fixing the image photographing system, the wireless transmitter, the battery, and the counterweight.

The image photographing system may include: a light source for irradiating light to a subject to be photographed; a lens for condensing light reflected by the subject to be photographed; and an image sensor for converting an image received via the lens into an electric signal.

The image photographing system may be disposed such that images are photographed in a direction opposite to the counterweight.

The lens may have an aperture angle of 45° to 180°.

The image photographing system may be disposed such that images are photographed in a direction toward the counterweight.

The counterweight may be a magnetic body.

The shell unit may be formed of one of a transparent resin and a transparent plastic material.

A string for controlling a position of the capsule-type image photographing apparatus may be connected to the shell unit.

The counterweight may have a plate shape, a globular shape, a partially cutaway globular shape, or a ring shape.

A lubricant may be interposed between the shell unit and the main body unit.

According to another aspect of the present invention, there is provided an endoscopy method using a capsule-type image photographing apparatus. The method includes: putting the capsule-type image photographing apparatus into a tested person's body through a tested person's mouth; moving the capsule-type image photographing apparatus to a desired position in the tested person's body while monitoring images transmitted from the capsule-type image photographing apparatus put in the tested person's body in real-time; and monitoring images transmitted from the capsule-type image photographing apparatus moved to the desired position.

The capsule-type image photographing apparatus may include a shell unit and a main body unit capable of freely rotating in the shell unit. The main body unit may include an image photographing system, a wireless transmitter, a battery, a counterweight for determining the center of gravity of the main body unit, and an encapsulant for fixing the image photographing system, the wireless transmitter, the battery, and the counterweight.

A lubricant may be interposed between the shell unit and the main body unit.

At least one of a first capsule-type image photographing apparatus for photographing long-distance regions and a second capsule-type image photographing apparatus for photographing short-distance regions may be used as the capsule-type image photographing apparatus.

A string for controlling a position of the capsule-type image photographing apparatus may be connected to the capsule-type image photographing apparatus.

After finishing endoscopy, the method may further include removing the capsule-type image photographing apparatus from the tested person's body through the tested person's mouth using the string.

The image photographing system may be disposed such that images are photographed in a direction opposite to the counterweight.

The image photographing system may be disposed such that images are photographed in a direction toward the counterweight.

A counterweight of the first capsule-type image photographing apparatus may be located in a direction opposite to a direction in which the image photographing system photographs images.

A counterweight of the second capsule-type image photographing apparatus may be located toward a direction in which the image photographing system photographs images.

The counterweight may be a magnetic body.

In order to move the capsule-type image photographing apparatus to the desired position in the tested person's body, a tested person's posture may be changed.

Alternatively, the tested person into which the capsule-type image photographing apparatus is put may be laid down in a magnetic field generator, and the capsule-type image photographing apparatus may be moved to the desired position in the tested person's body by controlling the intensity and direction of a magnetic field generated by the magnetic field generator. Also, after laying down the tested person in the magnetic field generator, the tested person's posture may be changed.

The counterweight may have a plate shape, a globular shape, a partially cutaway globular shape, or a ring shape.

MODE FOR INVENTION

Figure 1:
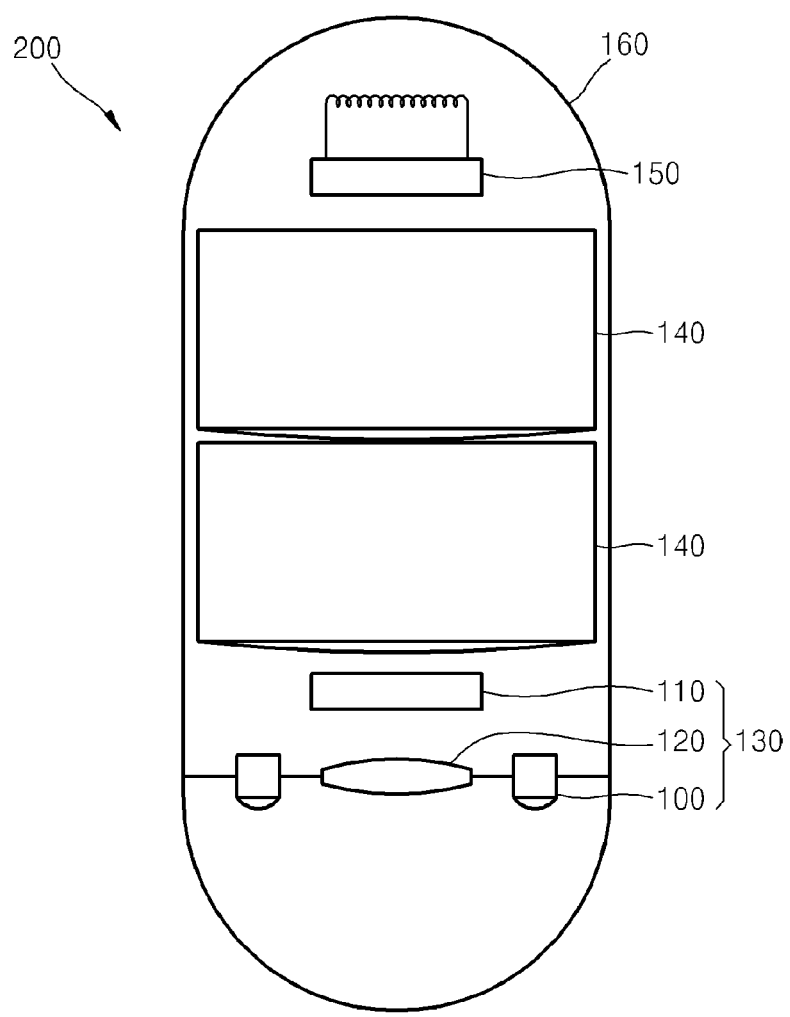
FIG. 1 is a cross-sectional view of a conventional capsule-type endoscope.

The present invention will hereinafter be described more fully with reference to the accompanying drawings, in which exemplary embodiments of the invention are shown. In the drawings, the sizes and shapes of components are appropriately controlled for clarity.

Initially, a capsule-type image photographing apparatus according to an embodiment of the present invention will be described.

Embodiment 1

Figure 2:
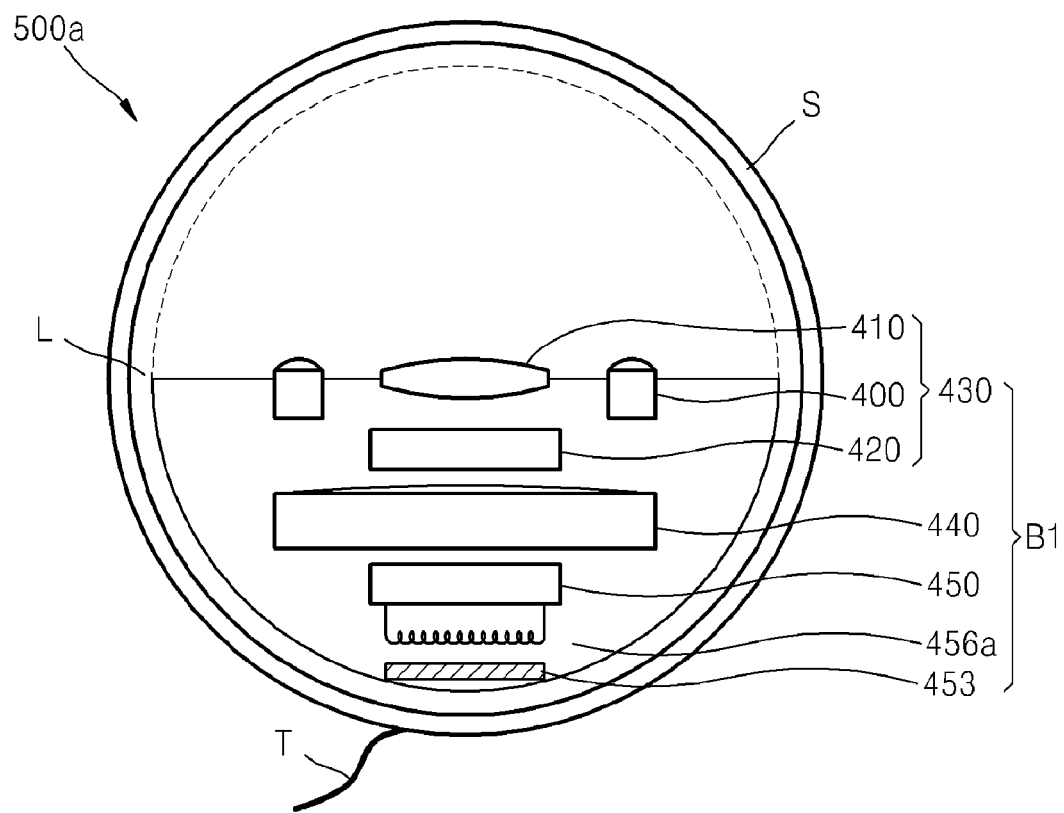
FIGS. 2 and 3 are cross-sectional views of capsule-type image photographing apparatuses according to embodiments of the present invention.

FIG. 2 is a cross-sectional view of a capsule-type image photographing apparatus (hereinafter referred to as a first capsule-type endoscope 500a) according to an embodiment of the present invention.

Referring to FIG. 2, the first capsule-type endoscope 500a includes a globular shell unit S and a main body unit B1. A lubricant L may be interposed between the globular shell unit S and the main body unit B1. Thus, the main body unit B1 may rotate freely in any direction in the globular shell unit S. The globular shell unit S may be formed of a transparent resin or a transparent plastic. The lubricant L may be coated on an internal surface of the globular shell unit S. The main body unit B1 includes an image photographing system 430, a battery 440, a wireless transmitter 450 for receiving an image from the image photographing system 430 and externally transmitting the image, a counterweight 453 located under the wireless transmitter 450, and an encapsulant 456a for encapsulating the above-described components 430, 440, 450, and 453. The counterweight 453 may be plate-shaped or globe-shaped. Due to the counterweight 453, the center of gravity of the main body unit B1 is located at the lowest portion thereof. Also, since the lubricant L is interposed between the globular shell unit S and the main body unit B1, even if the globular shell unit S rotates in any direction, the image photographing system 430 of the main body unit B1 included in the globular shell unit S may always face upward. However, a direction in which the image photographing system 430 photographs images may depend on the location of the center of gravity of the main body unit B1.

When the first capsule-type endoscope 500a is in a tested person's specific internal organ (e.g., the stomach), the counterweight 453 permits the image photographing system 430 to always photograph upward images in the stomach. Thus, under the influence of gravity, the first capsule-type endoscope 500a may be located on the bottom of the stomach and used to photograph upper portions of the stomach, that is, long-distance regions of the stomach. Also, when the tested person is rotated in a given direction, the image photographing system 430 may capture images of other regions of the stomach, for example, the sides and bottom of the stomach.

The main body unit B1 is disposed in a lower hemisphere of the globular shell unit S. Thus, the encapsulant 456a has a hemispheric structure. The image photographing system 430 includes a light source 400, a lens 410, and an image sensor 420. The light source 400 irradiates light to a subject to be photographed, for example, an inner wall of the stomach. The lens 410 condenses light reflected by the subject to be photographed. Also, the image sensor 420 converts an image received via the lens 410 into an electric signal. The lens 410 is interposed between the image sensor 420 and the globular shell unit S. Preferably, the lens 410 may be located on a surface of the encapsulant 456a. The light source 400 may be located around the image sensor 420 or the lens 410. A plurality of the light sources 400 may be disposed. The image sensor 420 may be a complementary metal oxide semiconductor (CMOS) image sensor or a charge coupled device (CCD) image sensor.

The image photographing system 430 is disposed such that the lens 410 is located in the center of a top surface of the hemispheric encapsulant 456a, that is, at the center of the globular shell unit S. The image photographing system 430 photographs images in an upward direction, and a photographed region corresponds to a region of the subject to be photographed, which is viewed through an upper hemisphere of the globular shell unit S. Accordingly, the upper hemisphere of the globular shell unit S may form an aperture of the image photographing system 430. Thus, an interior angle of the aperture of the image photographing system 430 may be 180° or less. Preferably, the interior angle of the aperture of the image photographing system 430 may range from 45° to 180°. In the case of a capsule-type endoscope shown in FIG. 3 according to another embodiment of the present invention, an interior angle of an aperture may be about 90°.

Embodiment 2

A capsule-type image photographing apparatus (hereinafter referred to as a second capsule-type endoscope 500b) according to another embodiment of the present invention has generally about the same construction as the first capsule-type endoscope 500a shown in FIG. 2, and thus only differences between the first and second capsule-type endoscopes 500a and 500b will now be described.

Figure 3:
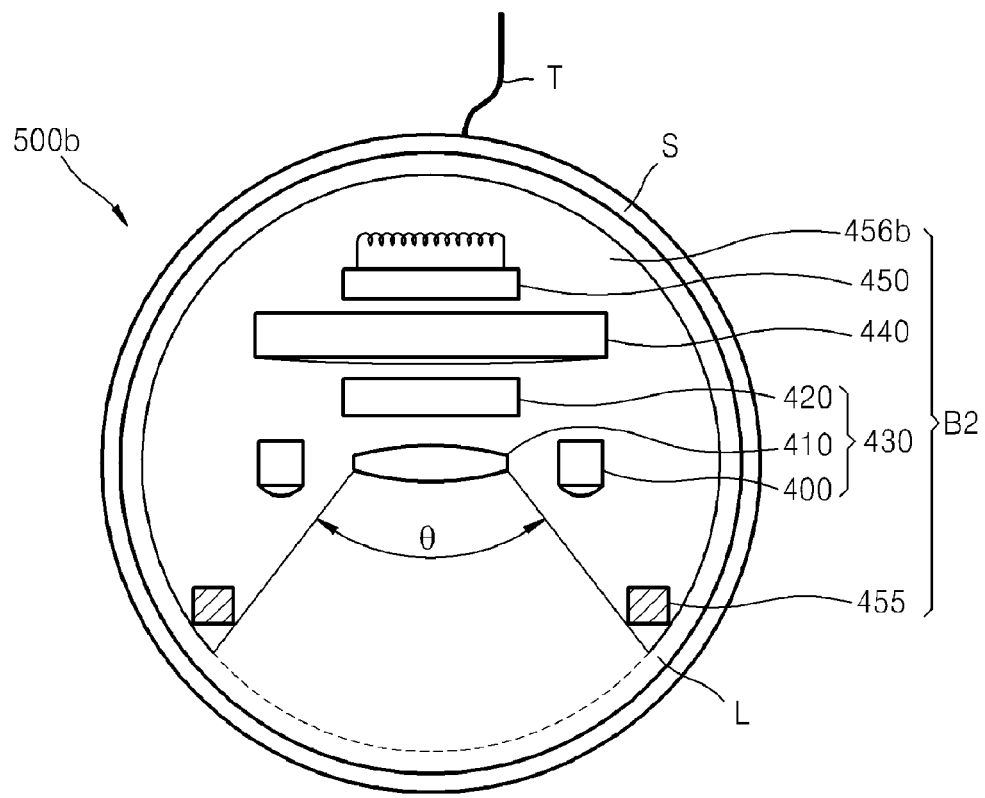

Referring to FIG. 3, a main body unit B2 of the second capsule-type endoscope 500b has the same construction as a resultant structure obtained by rotating the first capsule-type endoscope 500a shown in FIG. 2 except the counterweight 453 about a virtual line passing through the lens 410 and the light source 400 into the upper hemisphere of the globular shell unit S. Thus, in the main body unit B2 of the second capsule-type endoscope 500b, an image photographing system 430 is disposed below a wireless transmitter 450.

In the second capsule-type endoscope 500b, an encapsulant 456b for fixing and encapsulating respective components of the main body unit B2 takes up to 60% or more of an inner space of the globular shell unit S. In more detail, a region unoccupied by the encapsulant 456b in the globular shell unit S has a fan shape. Also, border lines of the encapsulant 456b are oblique lines that start from the edge of the lens 410 and go down toward an inner surface of the globular shell unit S. Therefore, an angle made between the border lines of the encapsulant 456b around the lens 410, that is, an aperture angle θ, may be about 90°.

The main body unit B2 of the second capsule-type endoscope 500b includes a counterweight 455. The counterweight 455 includes two or four symmetric objects, but it may have a ring shape. The counterweight 455 is located down below the image photographing system 430. More specifically, the counterweight 455 is inside the lowest edge of the encapsulant 456b. Accordingly, the center of gravity of the main body unit B2 is located below the image photographing system 430, and more specifically, below the lens 410 and near the inner surface of the globular shell unit S rather than near the lens 410.

As described above, since the center of gravity of the main body unit B2 is located below the lens 410 near the inner surface of the globular shell unit S, the image photographing system 430 always photographs downward images under the influence of gravity. Thus, when the second capsule-type endoscope 500b is in a tested person's specific internal organ (e.g., the stomach), a portion (e.g., the bottom of the stomach) contacted by the second capsule-type endoscope 500b can be proximately photographed. Also, when the tested person is rotated to bring the second capsule-type endoscope 500b into contact with a side or the top of the stomach, the second capsule-type endoscope 500b can proximately photograph the side or top of the stomach.

Meanwhile, in the first and second capsule-type endoscopes 500a and 500b, the counterweights 453 and 455 may be magnetic bodies. In this case, a direction in which the image photographing system 430 photographs images may be controlled by externally applying a magnetic field.

Also, a distance between the lens 410 and the image sensor 420 in the first capsule-type endoscope 500a for photographing long-distance images as shown in FIG. 2 may be shorter than that in the second capsule-type endoscope 500b for photographing short-distance images as shown in FIG. 3.

Further, a string T may be connected to each of the first and second capsule-type endoscopes 500a and 500b. The string T may be used to control the vertical moving speed of each of the first and second capsule-type endoscopes 500a and 500b. For example, by using the string T, each of the first and second capsule-type endoscopes 500a and 500b may be stopped at an arbitrary position between the top and bottom of the tested person's stomach. The string T may be formed of various materials.

Although not shown in the drawings, the first capsule-type endoscope 500a for photographing long-distance images may not necessarily include a hemispheric main body unit B1. That is, the encapsulant 456a of the main body unit B1 of the first capsule-type endoscope 500a may have the same shape as the encapsulant 456b of the main body unit B2 of the second capsule-type endoscope 500b.

Hereinafter, an endoscopy method using the above-described capsule-type endoscopes according to the present invention will be described.

The endoscopy method using a capsule-type endoscope according to the present invention may be categorized as either a method of controlling a photographing direction using gravity (hereinafter referred to as a gravity control method) or a method of controlling a photographing direction using a magnetic field (hereinafter referred to as a magnetic field control method).

To begin with, endoscopy using a gravity control method will now be described with reference to FIG. 4.

Figure 4:
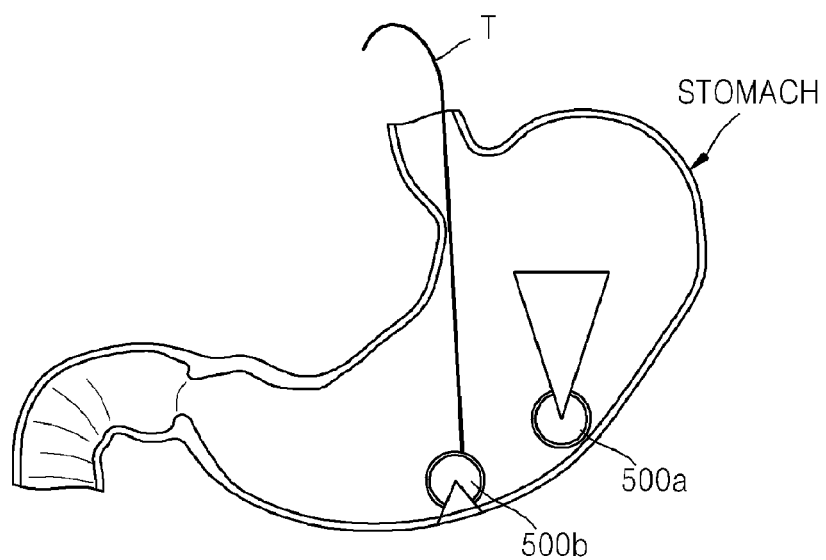
FIG. 4 is a schematic diagram for explaining endoscopy according to an embodiment of the present invention in which the motion of a capsule-type image photographing apparatus is controlled using gravity.

Referring to FIG. 4, the first capsule-type endoscope 500a shown in FIG. 2 and the second capsule-type endoscope 500b shown in FIG. 3 are put into a tested person's stomach through a tested person's mouth. When leaning the tested person's body in a specific direction, the first and second capsule-type endoscopes 500a and 500b move due to gravity according to a leaning direction and angle. In this case, a test may be performed while photographed images are being viewed in real-time using hospital equipment including a bed-type holder in which a tested person can lie down, for example, equipment for upper gastrointestinography (UGI) and image monitoring equipment. The bed-type holder may move in an arbitrary direction. For instance, the bed-type holder may rotate about a first axis. Also, the bed-type holder may rotate about a second axis orthogonal to the first axis. Accordingly, after the tested person is laid down on the bed-type holder and fixed thereto, the tested person may be rotated in a given direction.

Even if the first and second capsule-type endoscopes 500a and 500b move due to gravity, a direction in which the first capsule-type endoscope 500a photographs images is fixed in an upward direction, while a direction in which the second capsule-type endoscope 500b photographs images is fixed in a downward direction. Thus, both long-distance and short-distance regions can be photographed by moving the first capsule-type endoscope 500a for photographing the long-distance regions and the second capsule-type endoscope 500b for photographing the short-distance regions in desired directions in the tested person's stomach. In this case, the positions of the first and second capsule-type endoscopes 500a and 500b can be controlled more easily by use of the string T.

Endoscopy using a magnetic field control method will now be described.

Figure 5:
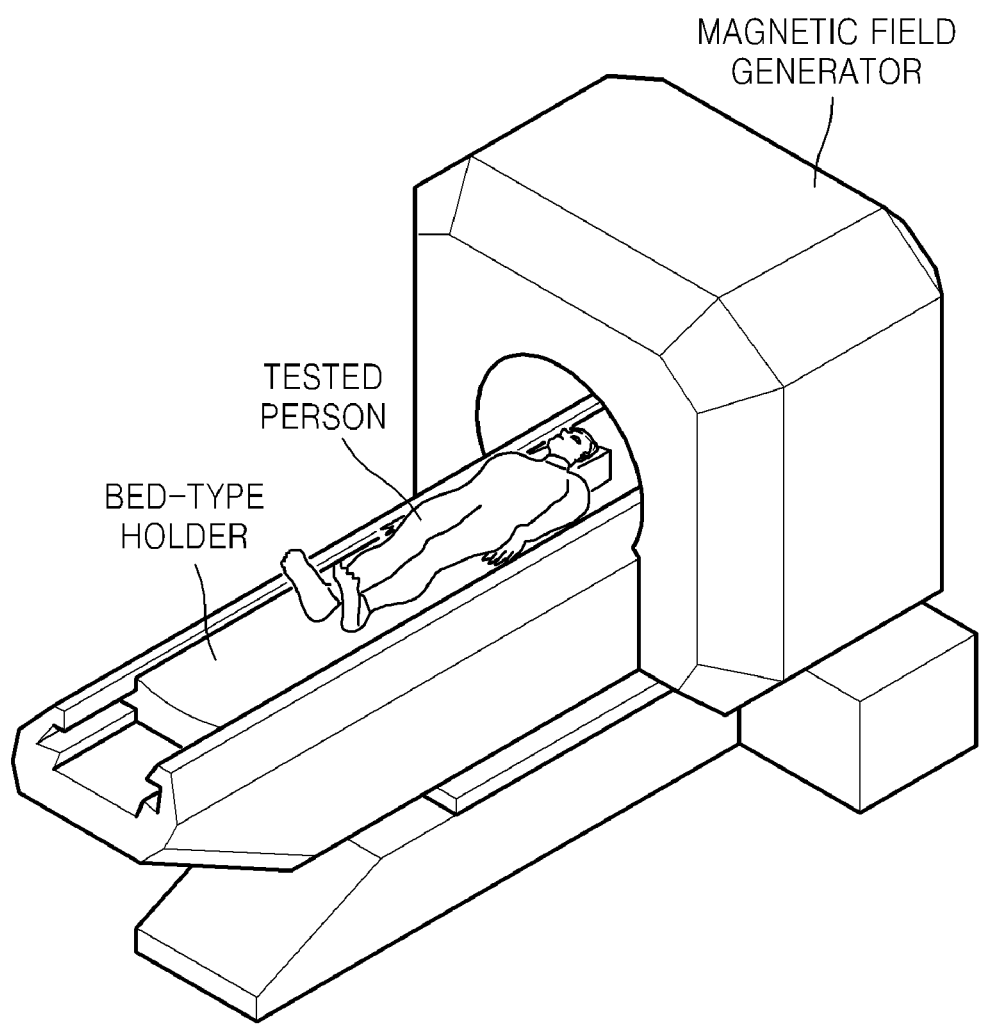
FIG. 5 is a schematic diagram for explaining endoscopy according to another embodiment of the present invention in which the motion of a capsule-type image photographing apparatus is controlled using a magnetic field.
Figure 6A:
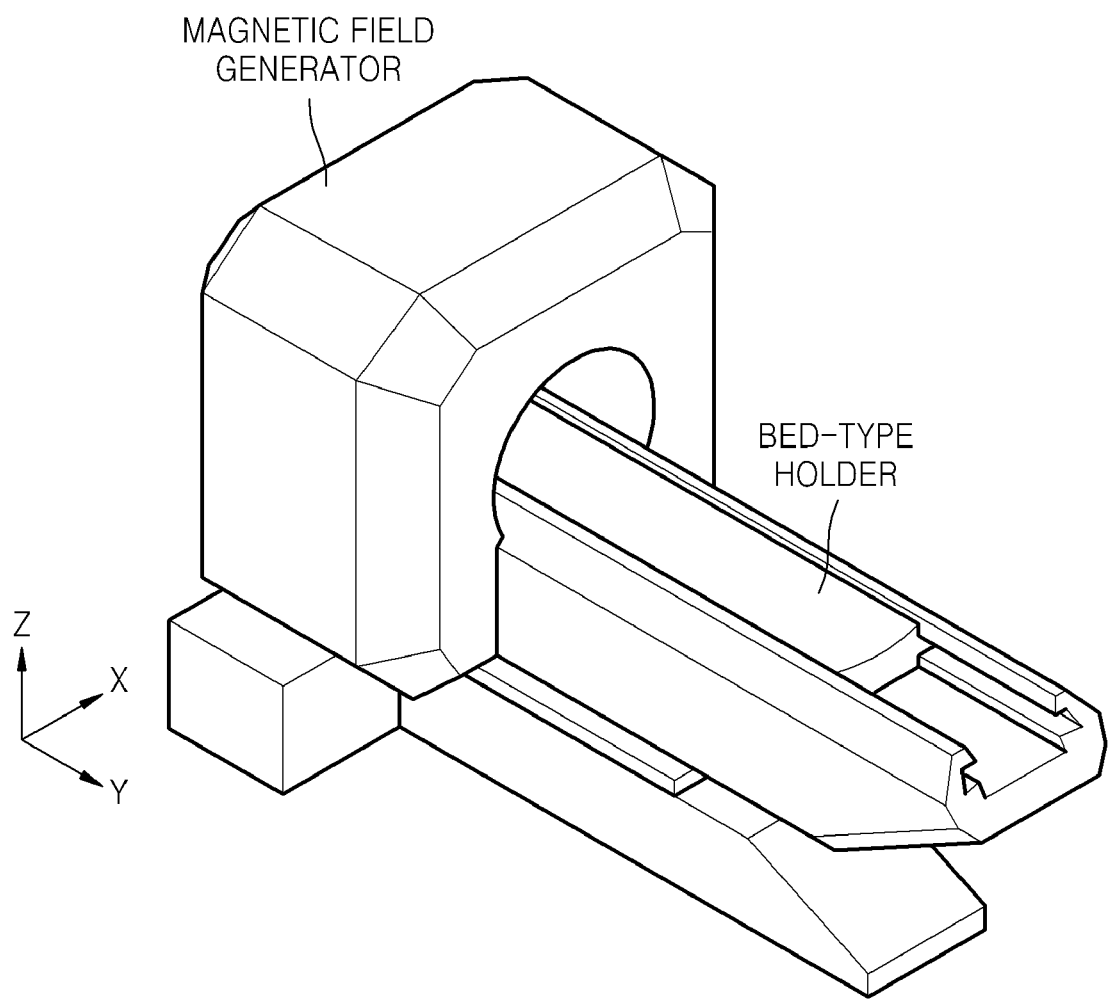
FIGS. 6A and 6B are respectively perspective views of a magnetic field generator before and after a bed-type holder is moved.
Figure 6B:
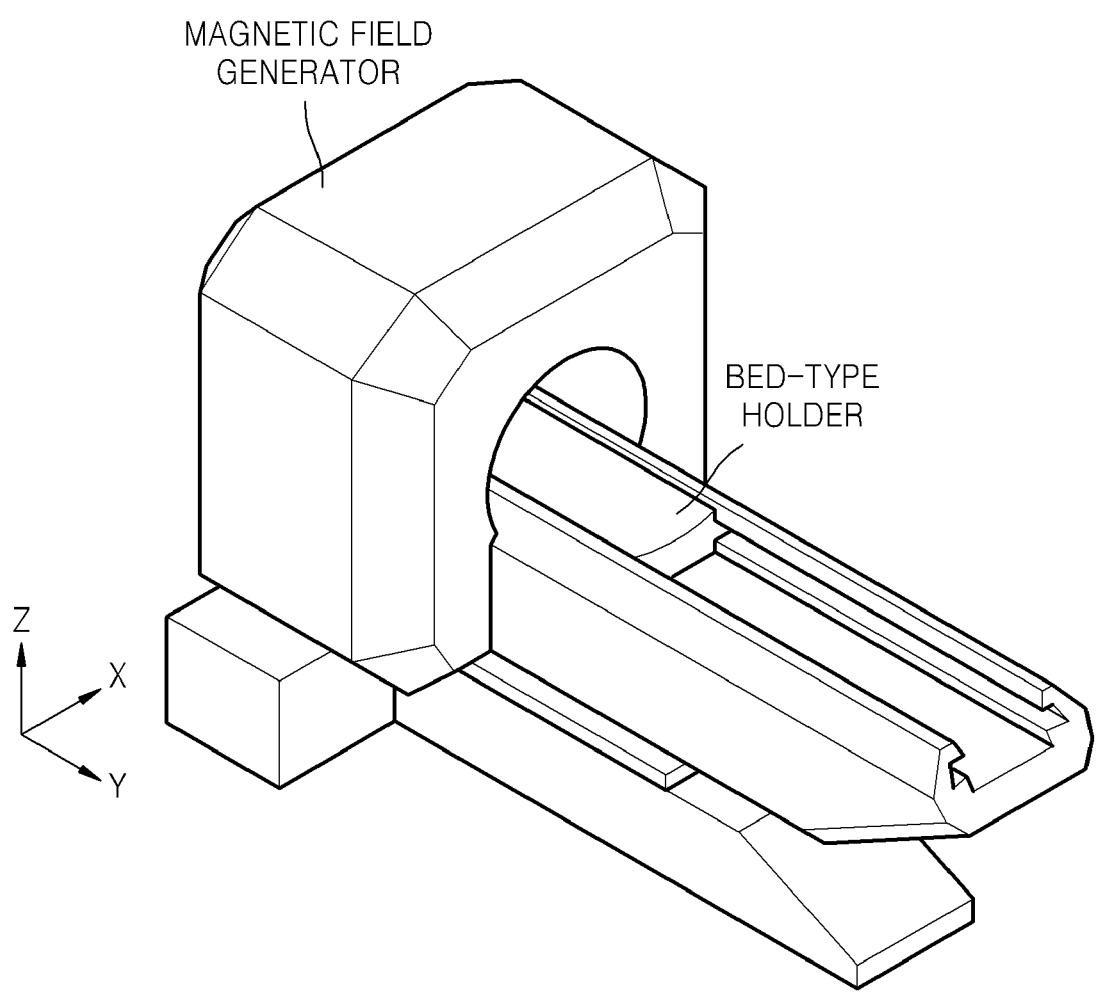
Figure 7A:
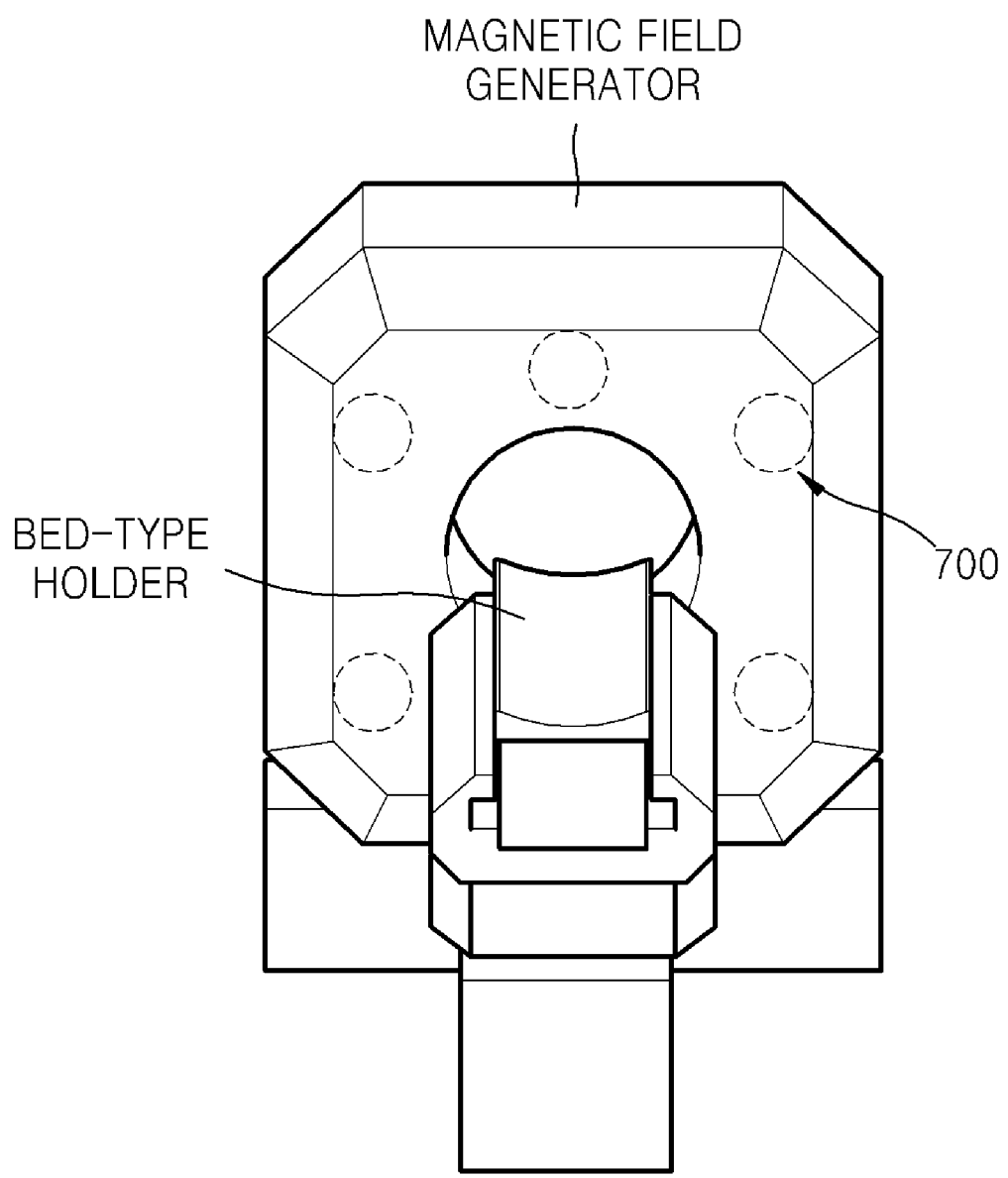
FIGS. 7A and 7B are respectively perspective views of front and rear portions of a magnetic field generator.
Figure 7B:
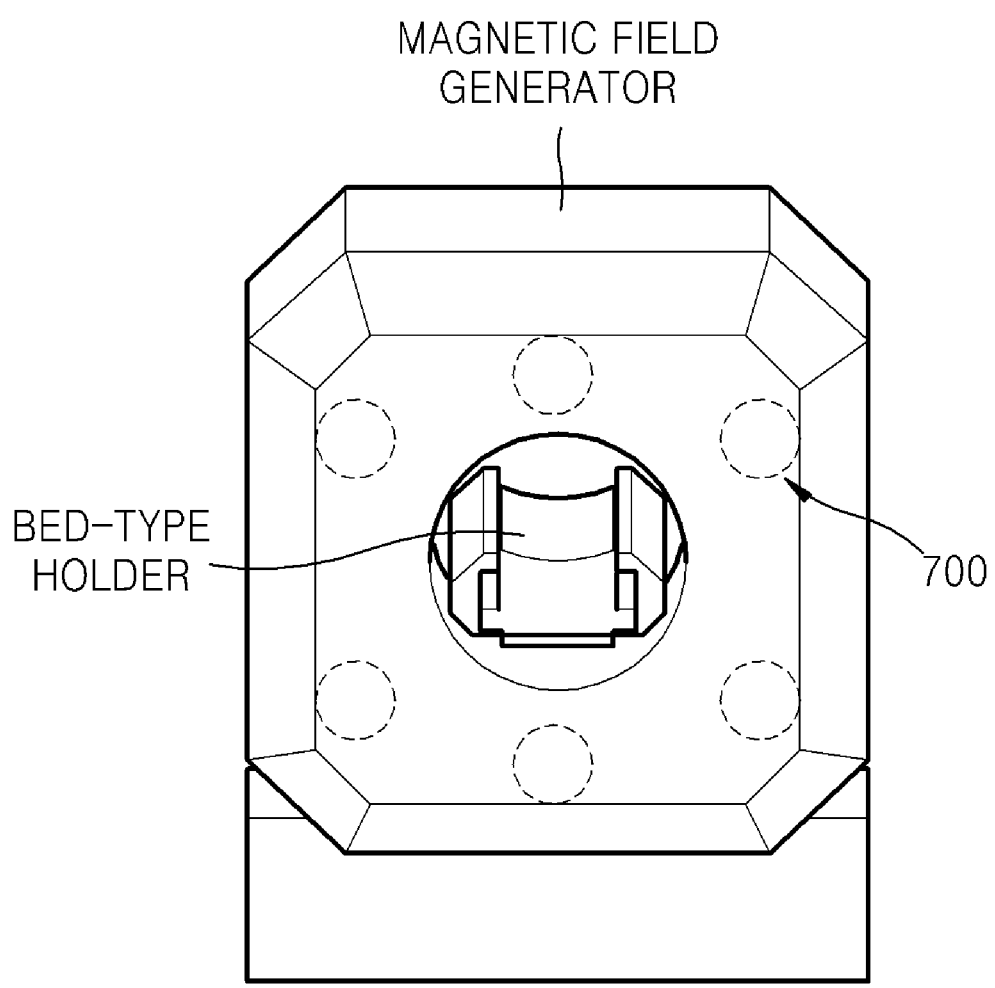

Initially, the first and/or second capsule-type endoscopes 500a and/or 500b including the counterweights 453 and/or 455 formed of magnetic bodies are put into a tested person's stomach, and the tested person is laid down on a bed-type holder of a magnetic field generator as shown in FIG. 5 and fixed thereto. Thereafter, the bed-type holder is moved such that a tested person's region to be tested is located inside the magnetic field generator. FIGS. 6A and 6B are respectively perspective views of the magnetic field generator before and after the bed-type holder is moved, and FIGS. 7A and 7B are respectively perspective views of front and rear portions of the magnetic field generator.

Subsequently, a sufficient magnetic field to move the first and/or second capsule-type endoscopes 500a and/or 500b according to the present invention is applied to the tested person in a given direction. Referring to FIGS. 7A and 7B, a plurality of coils 700 are formed in the magnetic field generator to generate a magnetic field. The coils may be formed such that the coil axis is parallel to a Y direction shown in FIG. 6A. In this case, the applied magnetic field is so feeble that it cannot be a physical or mental burden on the tested person.

By moving the first and/or second capsule-type endoscopes 500a and/or 500b into desired regions in the tested person by varying a direction in which a magnetic field is applied, images photographed by the first and/or second capsule-type endoscopes 500a and/or 500b are monitored in real-time. Also, as with the endoscopy using the gravity control method, a direction in which a magnetic field is applied may be fixed in a given direction, and the first and/or second capsule-type endoscopes 500a and/or 500b may be moved into desired regions by moving the bed-type holder.

The magnetic field generator and the method of operating the same described with reference to FIGS. 5 through 7B may be similar to or the same as a magnetic field generator and a method of operating the same, which have been disclosed in detail in Korean Patent No. 10-0457752. Therefore, the magnetic field generator and the method of operating the same will be better understood in detail by referring to Korean Patent No. 10-0457752.

When the above-described two endoscopy methods are performed using the first and/or second capsule-type endoscopes 500a and/or 500b with the strings T, after photographing desired images by moving the first and/or second capsule-type endoscopes 500a and/or 500b in a tested person's body, the first and/or second capsule-type endoscopes 500a and/or 500b may be taken out of the body through a tested person's mouth.

As described above, a capsule-type image photographing apparatus according to the present invention includes a globular shell unit and a main body unit capable of freely rotating in the globular shell unit. The main body unit includes an image photographing system and a member supporting the image photographing system and further includes a counterweight, which permits the image photographing system to photograph images in a direction toward the counterweight or in a direction opposite to the counterweight.

Therefore, by use of the capsule-type image photographing apparatus according to the present invention, desired regions of a tested person's internal organs can be photographed at long or short distances.

Also, when using both the two capsule-type image photographing apparatuses according to the present invention, long and short distance regions of the tested person's internal organs can be photographed at the same time.

Furthermore, according to the present invention, the position of a capsule-type image photographing apparatus is controlled using gravity and/or a magnetic field, so that desired images can be captured by moving the capsule-type image photographing apparatus to a desired position in the tested person's internal organs. Moreover, by connecting a string to the capsule-type image photographing apparatus, the vertical moving speed of the capsule-type image photographing apparatus can be controlled, and the capsule-type image photographing apparatus can be rapidly removed from the tested person.

As a consequence, a wide internal organ, such as the stomach, can be tested more easily, and a tested person feels little pain unlike when a tube-type endoscope is used. Also, the tested person can observe photographed images in real-time, so that a test can be finished in a short amount of time and ease an economical burden for the tested person.

While the present invention has been particularly shown and described with reference to exemplary embodiments thereof, the invention may be embodied in many different forms and should not be construed as being limited to the embodiments set forth herein. For example, those skilled in the art to which the present invention pertains can make various changes in the element of the capsule-type endoscope of the present invention, or can modify position relations between the elements thereof. In addition, the method of photographing the inside of human body, according to the present invention can also be used for examination of other organs besides stomach. Therefore, the scope of the invention is defined not by the exemplary embodiments of the invention but by the following claims.

The invention claimed is:

1. A capsule-type image photographing apparatus comprising:
   a shell unit having a globular shape; and
   a main body unit capable of freely rotating in the shell unit, the main body unit comprising an image photographing system, a wireless transmitter, a battery, a counterweight for determining the center of gravity of the main body unit, and an encapsulant for fixing the image photographing system, the wireless transmitter, the battery, and the counterweight, and
   the entire main body unit being a partially globular shape and partially occupying the inner space of the shell unit, the entire main body unit having a cross-section of a circle with a sector cut out, the sector having a fan shape, and
   wherein the image photographing system is configured such that images are photographed in a downward direction with respect to the counterweight, and an internal surface of the shell unit is coated with a lubricant, and the image photographing system comprises a lens, the lens being located at a center portion of the inner space of the shell unit and on a surface of the encapsulant, the entire main body unit comprises a hemispherical upper portion and a lower portion, the lower portion extending from the hemispherical upper portion toward a lower end of the shell unit, border lines of the lower portion being oblique lines that start from the lens and go down toward an internal surface of the shell unit, and the counterweight is located in an edge portion of the lower portion of the main body.

2. The apparatus of claim 1, wherein the image photographing system comprises:
   a light source for irradiating light to a subject to be photographed;
   the lens for condensing light reflected by the subject to be photographed; and
   an image sensor for converting an image received via the lens into an electric signal.

3. The apparatus of claim 2, wherein the lens has an aperture angle of 45° to 180°.

4. The apparatus of claim 1, wherein the counterweight is a magnetic body.

5. The apparatus of claim 1, wherein the shell unit is formed of one of a transparent resin and a transparent plastic material.

6. The apparatus of claim 1, wherein a string for controlling a position of the capsule-type image photographing apparatus is connected to the shell unit.

7. The apparatus of claim 1, wherein the counterweight has a shape selected from the group consisting of a plate shape, a globular shape, a partially cutaway globular shape, and a ring shape.

8. A capsule-type image photographing apparatus comprising:
   a first capsule-type endoscope for short-distance photographing; and
   a second capsule-type endoscope for long-distance photographing,
   wherein the first capsule-type endoscope comprises,
      a first shell unit having a globular shape; and
      a first main body unit capable of freely rotating in the first shell unit,
      the first main body unit comprising a first image photographing system, a first wireless transmitter, a first battery, a first counterweight for determining the center of gravity of the first main body unit, and a first encapsulant for fixing the first image photographing system, the first wireless transmitter, the first battery, and the first counterweight, and
   the entire first main body unit being a partially globular shape and partially occupying the inner space of the first shell unit, the entire first main body unit having a cross-section of a circle with a sector cut out, the sector having a fan shape, and
   wherein the first image photographing system is configured such that images are photographed in a downward direction with respect to the first counterweight, and an internal surface of the first shell unit is coated with a first lubricant, and
   wherein the second capsule-type endoscope comprises,
      a second shell unit having a globular shape; and
      a second main body unit capable of freely rotating in the second shell unit,
      the second main body unit comprising a second image photographing system, a second wireless transmitter, a second battery, a second counterweight for determining the center of gravity of the second main body unit, and a second encapsulant for fixing the second image photographing system, the second wireless transmitter, the second battery, and the second counterweight, and
   the entire second main body unit being a partially globular shape and partially occupying the inner space of the second shell unit, the entire second main body unit being hemispherical, and
   wherein the second image photographing system is configured such that images are photographed in an upward direction with respect to the second counterweight, and an internal surface of the second shell unit is coated with a second lubricant,
   wherein the first capsule-type endoscope has a first contact region which contacts an internal organ, and the first capsule-type endoscope is configured to photograph toward the first contact region, and
   the second capsule-type endoscope has a second contact region which contacts the internal organ, and the second capsule-type endoscope is configured to photograph in an upper direction with respect to the second contact region.

* * * * *